(12) United States Patent
Bijl et al.

(10) Patent No.: US 6,441,208 B2
(45) Date of Patent: Aug. 27, 2002

(54) PREPARATION OF MICROBIAL POLYUNSATURATED FATTY ACID CONTAINING OIL FROM PASTEURIZED BIOMASS

(75) Inventors: Hendrik Louis Bijl, Vlaardingen; Johannes Hendrik Wolf, Delft; Albert Schaap, Barendrecht; Johannes Martinus Jacobus Visser, Amersfoort, all of (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/764,087

(22) Filed: Jan. 19, 2001

Related U.S. Application Data

(62) Division of application No. 08/821,026, filed on Mar. 19, 1997, now Pat. No. 6,255,505
(60) Provisional application No. 60/015,110, filed on Apr. 10, 1996.

(30) Foreign Application Priority Data

Mar. 28, 1996 (EP) ............................................. 96200835
Mar. 28, 1996 (EP) ............................................. 96200837

(51) Int. Cl.$^7$ ................................................. C11B 1/00
(52) U.S. Cl. ........................... 554/8; 554/20; 435/132; 435/134; 435/171; 435/254.1; 435/257.1
(58) Field of Search ..................... 554/8, 20; 435/132, 435/134, 171, 254.1, 257.1

(56) References Cited

U.S. PATENT DOCUMENTS

| | | |
|---|---|---|
| 4,857,329 A | 8/1989 | Sako et al. |
| 5,340,594 A | 8/1994 | Barclay et al. |
| 5,407,957 A | 4/1995 | Kyle et al. |
| 5,411,873 A | 5/1995 | Adams et al. |
| 5,539,133 A | 7/1996 | Kohn et al. |

FOREIGN PATENT DOCUMENTS

| | | |
|---|---|---|
| DD | 150 627 A | 9/1981 |
| DE | 19 23 529 A | 12/1969 |
| EP | 0 155 420 | 9/1984 |
| EP | 0 223 960 A2 | 9/1986 |
| EP | 0 276 541 A2 | 9/1987 |
| EP | 0 322 227 A | 6/1989 |
| EP | 0 520 624 A | 12/1992 |
| EP | 0 522 470 | 1/1993 |
| FR | 2 210 662 A | 7/1974 |
| GB | 1 466 853 A | 3/1977 |
| WO | 89/05469 | 9/1987 |
| WO | 90/13656 A | 11/1990 |
| WO | 91/07498 | 5/1991 |
| WO | 91/11918 | 8/1991 |
| WO | 91/14427 | 10/1991 |
| WO | 91/16443 A | 10/1991 |
| WO | WO 92 12711 A | 8/1992 |
| WO | 92/13086 | 8/1992 |
| WO | 92/13086 A | 8/1992 |

OTHER PUBLICATIONS

Applied and Environmental Microbiology, 58 (7). 1992 2196–2200.

(List continued on next page.)

Primary Examiner—Deborah D Carr
(74) Attorney, Agent, or Firm—Morrison & Foerster LLP

(57) ABSTRACT

The present invention discloses a microbial polyunsaturated fatty acid(PUFA)-containing oil with a high triglyceride content and a high oxidative stability. In addition, a method is described for the recovery of such oil from a microbial biomass derived from a pasteurized fermentation broth, wherein the microbial biomass is subjected to extrusion to form granular particles, dried and the oil then extracted from the dried granules using an appropriate solvent.

31 Claims, 4 Drawing Sheets

OTHER PUBLICATIONS

Journal of the American Oil Chemists' Society, 70 (2) 1993 119–123.

Database WPI Week 8928 Derwent Publications Ltd., London GB AN 89–201959.

Database WPI Week 8848 Derwent Publications Ltd., Condon GB AN 88–341507.

Jareonkitmongkol et al., Applied and Environmental Microbiology, 58(7), pp. 2196–2200 (1992).

Jareonkitmongkol et al., JAOCS, 70(2), pp. 119–123 (1993).

Yamada, H. et al., "Production of Dihomo–γ–linolenic Acid, Arachidonic Acid and Eicosapentaenoic Acid by Filamentous Fungi," Chapter 7, in: *Industrial Applications of Single Cell Oils,* Kyle, D.J., et al., eds., pp. 118–138, 1989.

PREPARATION OF MICROBIAL POLYUNSATURATED FATTY ACID CONTAINING OIL FROM PASTEURIZED BIOMASS

This application is a division of application Ser. No. 08/821,026, filed Mar. 19, 1997, now U.S. Pat. No. 6,255, 505, which claims benefit of Provisional application Ser. No. 60/015,110, filed Apr. 10, 1996.

FIELD OF THE INVENTION

The present invention relates to a polyunsaturated fatty acid-(PUFA) containing oil, especially to a pure and stable microbial oil containing at least one polyunsaturated fatty acid. This oil can be obtained from a biomass or fermentation broth that has been subjected to pasteurisation.

BACKGROUND OF THE INVENTION

There has been a growing tendency to include lipid products containing polyunsaturated fatty acids derived from fermentation processes in various foodstuffs. Of importance is the recently established need to incorporate polyunsaturated fatty acids in infant formula.

Various processes have been described for the fermentative production of lipid or oil containing polyunsaturated fatty acids. Examples are EP-A-0155420 for the production of γ-linolenic acid-(GLA) containing lipid from Mortierella; EP-A-0223960, EP-A-0276541 and WO-A-92/13086 for the production of arachidonic acid-(ARA) containing oil from Mortierella and/or Pythium; WO-A-91/07498 and WO-A-91/11918 for the production of docosahexaenoic acid-(DHA) containing oil from *Czypthecodinium cohnii* or Thraustochytrium, and WO-A-91/14427 for the production of eicosapentaenoic acid-(EPA) containing oil from Nitzschia; and U.S. Pat. No. 5,539,133 for production of ARA and EPA from microalgae.

Typically, a microbial species producing a lipid containing the desired polyunsaturated fatty acid(s) is cultured in a suitable medium, the biomass is then harvested and pretreated to enable subsequent extraction of lipid from the microbial biomass with a suitable solvent. The thus-extracted lipid is in a crude form and so is often subjected to several refining steps.

The pretreatment of the wet biomass cake is usually by drying, such as spray drying or lyophilization and/or by mechanical disintegration, such as homogenisation or milling. Drying of the biomass is desirable in order to reduce the amount of solvent and to prevent troublesome emulsions. If an oxidation- and thermo-sensitive lipid, such as a polyunsaturated fatty acid-containing lipid, needs to be isolated, special care needs to be taken to ensure that exposure to unfavorable conditions, which stimulate oxygen-induced degradation, is avoided as much as possible. However, the biomass pretreatment methods used in the art do not avoid such unfavorable is conditions.

Yamada et al, Industrial applications of single cell oils, Eds. Kyle and Ratledge, 118–138 (1992) describe an arachidonic acid-containing oil purified from *Mortierella alpina* with a triglyceride content of 90%. In the recovery process, the harvested biomass is dried and crushed by a ball mill prior to hexane extraction. This method also does not minimise exposure to unfavorable conditions.

Thus, polyunsaturated fatty-acid-containing lipids isolated from microbial biomass according to methods known in the art are exposed to oxidation-stimulating conditions which negatively affect the quality of the oil.

DESCRIPTION OF THE INVENTION

According to a first aspect of the present invention there is provided a microbial oil, comprising at least one polyunsaturated fatty acid (PUFA), which has a triglyceride content of greater than 90%. This oil has been found to be particularly stable in comparison with prior art PUFA-containing oils. The PUFA is produced by one or more microorganisms, suitably in a fermentation process. The PUFA is recovered by various process steps, from the biomass, which is essentially the material resulting from the fermentation process in which the PUFA is produced.

Since the oil of the present invention can be microbially derived, it will be appreciated that this oil does not cover synthetic oils. Although not wishing to be bound by theory, the applicant believes that there may be a number of explanations as to why the oil of the present invention is more stable than those described before the present invention.

The oil may contain one or more compounds that were present in the biomass. While more of these compounds may act as an anti-oxidant. Alternatively or in addition, one or more of the compounds may inactivate (partially, or at least inhibit) one or more oxidising (or pro-oxidant) substances present in the oil.

A number of substances may be responsible for degradation of PUFA containing oils. These include metals, that may act as catalysts, for example copper, iron and/or zinc. Other, similar metals, may act as radical initiators. Other degrading influences are light and heat. There may be one or more substances that may, for example, may be able to complex with one of these metals, or they may act as a radical scavenger.

Alternatively, the process for obtaining the oil of the invention may remove one or more oxidative or oxidation-causing substances that may have originally been present in the biomass.

It is believed that degradation is particularly high when the PUFA is ARA, and therefore a substance in the oil may inhibit or prevent degradation of this PUFA.

The process of obtaining the oil of the invention, which will be described in more detail later, can involve the formation of a granular particulate form, or even dried granules, which may render the PUFA inside the granules or granular forms less accessible to the atmosphere, and in particular oxygen, thereby reducing the chances of oxidation.

In the process of the invention the sterol content maybe reduced, so that the maximum amount of sterols (such as 5-desmosterol) is 1.5% by weight.

The oil may therefore contain one or more radical inhibitors, radical scavengers and/or antioxidants.

The present invention thus relates to a microbial polyunsaturated fatty acid(PUFA)-containing oil with a high triglyceride content (e.g. at least 90%), and a high Pancimat induction time (e.g. at least 5 hours at 80° C.). The polyunsaturated fatty acid can be a C18, C20 or C22 ω-3 and C18, C20, or C22 ω-6 polyunsaturated fatty acid. Preferably it is a C20 or C22 ω-3, or a C20 ω-6 polyunsaturated fatty acids. In particular the PUFA is arachidonic acid (PUFA), eicosapentaenoic acid (EPA) docosahexaenoic acid (DHA). Examples of such oils are arachidonic acid-containing oil from Mortierella or a docosahexaenoic acid-containing oil from Czypthecodinium.

The oil of the invention can advantageously be used in foods, foods stuffs or food compositions or serve as a nutritional supplement, for humans as well as for animals. In addition, the oil of the invention can be used in cosmetics. The granular particles or granules may find use as a food or feed composition or supplement.

The oil of the present invention contains one or more polyunsaturated fatty acids and can have a high triglyceride content. This oil has a much higher oxidative stability than the microbial polyunsaturated fatty acid-containing oils described in the art.

The oil of the invention preferably has the following characteristics. It has a triglyceride content >90%, preferably a triglyceride content ≧93%. However, suitably the triglyceride content is ≧95%, optionally a triglyceride content ≧97%. It may further have a Rancimat induction time which is ≧5 hours at 80° C., preferably an induction time of 5–16 hours at 80° C. More suitably it can have an induction time of 7–16 hours at 80° C., optionally an induction time of 10–16 hours at 80° C. The Rancimat induction times are measured at a temperature of 80° C., since this temperature is better suited for oils containing polyunsaturated fatty acids. When measured at 100° C., the oil of the invention may have an induction time of from 3 to 5 hours.

It should be noted that the Rancimat induction time of the oil of the invention is measured without the presence of exogenously added stabilizing compounds, such as antioxidants. Obviously, the presence of stabilizing additives in an oil will increase its Rancimat induction time. Stabilizing additives, such as antioxidants, may originate from additions to certain steps of the oil recovery process, for instance to the medium wherein the microorganism is cultured, or from additions to the oil itself. The Rancimat test involves heating the substance, while air is blown over it. If the substance oxidises, then its weight increases, and usually oxidation occurs relatively rapidly after a particular time. This time therefore can give an indication of the stability, against oxidation, of the substance.

Additional characteristics of the oil of the invention may include a low diglyceride content, preferably below 2%, and/or a low monoglyceride content, preferably below 0.1%. It may have a light color, a low level of off-flavors and/or a low anisidine value (anisidine is a test for aldehydes, a product of degradation by oxidation).

The anisidine value typically varies from 0.1 to 5, preferably from 0.1 to 2, more preferably from 0.1 to 1. The colour of the oil of the invention is typically yellow to light yellow.

The microbial oil of the invention is typically one which predominantly (or only) contains one particular polyunsaturated fatty acid, but which may additionally contain lesser amounts of other polyunsaturated fatty acids. The present invention also contemplates microbial oils in which more than one polyunsaturated fatty acid is present.

The polyunsaturated fatty acids that maybe present in the microbial oil of the invention are C20 ω-3 and C18, C20 and C22 ω-6 polyunsaturated fatty acids. In particular they include γ-linolenic acid (GLA) dihomo-γ-linolenic acid (DLA) arachidonic acid (ARA), eicosapentaenoic acid (EPA) and docosahexaenoic acid (DHA).

The microbial biomass from which the oil of the invention can comprise, or originate from, any type of microorganism able to produce a PUFA-containing oil, for example a bacterium, a yeast, a fungus or an algae (or a mixture thereof).

For example, oil of the invention can comprise docosahexaenoic acid (DHA) preferably obtained from algae or fungi. Algae include dinoflagellates (e.g. those of the genus) Cxypthecodiniun. The fungus can be of the genus Mucorales, e.g. Thraustochytrium, γ-lizolenic acid(GLA), dihomo-γ-linolenic or arachidonic acid (AR) preferably obtained from fungi, such as Mortierella, Pythium or Entomophthora, or an eicosapentaenoic acid(EPA)-containing oil, preferably isolated from algae, such as Poxphyridium or Nitzschia. Typically, the oils obtained from these organisms predominantly contain one particular polyunsaturated fatty acid. However, they can additionally contain other polyunsaturated fatty acids in lesser amounts.

The present invention also relates to a method of isolating the polyunsaturated fatty acid-containing oil of the first aspect of the invention from microbial biomass; here the microbial biomass can be pretreated before extraction of the oil. Due to the relatively mild conditions of the pretreatment process, the thermo- and oxidation-sensitive polyunsaturated fatty acids present in the oil may not be exposed to conditions causing degradation.

Thus, according to a second aspect of the present invention, a process is provided for obtaining an oil comprising at least one polyunsaturated fatty acid (PUPA) from a microbial biomass (comprising organisms that have produced the PUFA), the process comprising:

a) providing, or obtaining, a biomass with a dry matter content of from 25 to 80%;

b) granulating the biomass into granular particles;

c) drying the granular particles to give dried granules; and d) extracting or isolating the oil from the dried granules.

Preferably, the particulate granular form has an average dry matter content of from 30 to 70%. The dried granules resulting from (c) suitably have an average dry matter content of at least 80%.

In a third aspect of the present invention there is provided a process for the isolation of one or more compounds from a microbial biomass, the process comprising:

a) culturing microorganisms in a fermentation broth under conditions whereby the compound is produced (by the microorganisms);

b) pasteurising either the fermentation broth or a microbial biomass derived from the broth; and c) extracting, isolating or recovering the compound from the microbial biomass.

The pasteurisation in (b) is intended to at least partially inactivate one or more compound degrading substance(s) that may be present in the biomass or broth. Such substances can include proteins, such as enzymes (e.g. proteases). In particular, one is seeking to at least partially inactivate lipases, phospholipases and/or lipoxygenases.

The compound preferably comprises a triglyceride, such as one of the PUFAs previously mentioned.

The pasteurisation will usually finish the fermentation. Preferably, this pasteurisation takes place before any granulating (or crumbling or kneading). Suitably, pasteurisation is performed on the fermentation broth, although it can be performed on the microbial biomass obtained from the broth.

By pasteurisation it is thought that at least some of the substances that can cause degradation of the compound (such as a PUFA) can be avoided. This pasteurisation may at least contribute to the high quality PUFAs that can be obtained by the present invention.

Thus, pasteurisation can be advantageous because not only may it kill the microorganism, but more importantly it can inactivate one or more enzymes that can adversely affect the compound. For example, pasteurisation may inactivate various lipases, and these may cleave fatty acids off a triglyceride backbone. This is disadvantageous for PUFAs where a high triglyceride content is preferred.

After pasteurisation, but before extraction in (c), one may perform granulating ( to give granular particles) and drying the granular particles as described above in stages (b) and (c) in the second aspect of the invention. Preferred features of one aspect of the invention are equally applicable, where appropriate, to other aspects.

In the process of the invention, the microorganism is first fermentated under conditions that allows production of the polyunsaturated fatty acid or acids to be produced. Such fermentation processes are well known in the art: the micro organism is usually fed with a carbon and nitrogen source, along with a number of additional chemicals or substances that allow growth of the micro organism and/or production of the PUFA. Suitable fermentation conditions are presented in Example 22.

The resulting material from fermentation (which is often called the broth) can then be filtered, or otherwise treated to remove at least part of the aqueous component. Suitably a large proportion of the water is removed, in order to obtain a biomass cake. The biomass at this stage preferably has a dry matter content of from 25 to 80%. The biomass can then be granulated into granular particles. This is preferably achieved by extrusion. However, whichever technique for granulation is chosen, which is preferable that cell disruption is either prevented or minimised. The granular particles can then be dried. The granules can significantly increases the efficiency of the subsequent drying step. The resulting (dried) granules are then particularly suitable for immersion or percolation extraction. The particle sizes of the granules can be adjusted for optimal drying and extraction additions.

The granulation conditions (such as those of an extrusion process) are preferably selected so that they minimise disruption of the microbial cell. This can increase resistance to degradation since the undisrupted cell is often the best form of protection against oxidative degradation of the intracellularly located polyunsaturated fatty acid.

Preferably, the PUFA is extracted from the dried granules using a solvent. Any suitable solvent known to a person skilled in the art can be employed. However, suitably a non-polar solvent is used, for example a $C_{1-6}$ alkane, for example hexane. It is also possible to use solvents in a super critical state, for example liquid carbon dioxide.

The process of the invention can enable a cost effective and efficient extraction of the PUFA oil, and provide an oil of a particularly high quality. For example, the dried granular form (of the biomass) allows one to use the percolation extraction process, which is particularly efficient. In addition, the granules allow the use of a relatively low temperature for extraction, which does not necessarily decrease the yield of the PUPA. Furthermore, the dried granules may require reduced amounts of solvent for the extraction process. An additional advantage is that the release of the used solvent from the biomass can be achieved more efficiently (this process is often referred to as desolventising toasting).

The residue resulting after (solvent) extraction (and even after desolventising toasting) can be used as a feed stuff or a feed component (such as for animals).

The PUFA (oil) which has been extracted can be used in that state without further processing, or it can be subjected to one or more further refining steps. Since the PUFA oil that is extracted from the dried granules is of a relatively high quality, any subsequent refining that is necessary is not only made easier, but can be minimised. Refining of the oil can be performed using standard techniques. For example, the oil can be subjected to degumming, deacidification, bleaching and/or deodorising. The PUFA containing oil of the present invention may have a high triglyceride content and/or high oxidative stability. It is particularly suitable for nutritional purposes. It can therefore be added to foods (either to the final foodstuff or added during the preparation of the foodstuff). It may serve as a nutritional supplement, for example if encapsulated in a suitable capsule, for example a gelatine capsule. The PUFA oil can be therefore used in food compositions either for humans or animals. Examples include milk, health drinks, and bread. The oils of the invention are particularly suitable for inclusion in infant formula. Furthermore, the oils can be used in cosmetics.

A third aspect of the invention therefore relates to a composition which comprises the microbial oil of the first aspect. This composition may be a food or feed stuff or a nutritional supplement, either for humans and/or animals. Such a composition, if a food composition, is preferably an infant formula. Alternatively, it may be a cosmetic composition.

By using dried granules of the biomass a higher yield than expected of the compound to be isolated can be achieved. This is thought to be due to the structure of the granules which can maximise access of the solvent to be used for the extraction. Of course, if the particles are too large, then the surface area may be lower, resulting in a correspondingly lower yield. However, the particles should not be too small otherwise they may clog the filter that is used during extraction. For this reason, the process of the invention does not include a milling, flaking or comminuting step or stages.

The water content at various stages can also influence yields. Too high a dry matter content, and the biomass will crumble and may form fines or dust, which is disadvantageous if a filtration extraction method is employed. However, too high a water content and one obtains a slurry that is too wet to be made into granules.

Processes for granulating matter are known in the art. However, they are often combined with milling or flaking at some stage, which gives the disadvantages as discussed above. In the present invention, it is the dried granules that are used for extraction of the compound, and not a milled or flaked form. In addition, by granulation, damage to the cells in the biomass may be minimized, which again can help increase yields of the compound. In U.S. Pat. No. 5,340,594 extrusion of a biomass is disclosed, but here the extruded form is used as an animal feed: there was no appreciation that the granular form would give high yields on extraction of a particular compound from that granular form.

By processing the biomass into granular particles, one can assist the drying process. Drying can be considerably easier and more efficient after the biomass has been processed into a granular form.

In addition, the dried granules have been found to be particularly stable, especially at ambient or room temperatures. The biomass can be stored for a considerable length of time in this form, without degradation. Although not wishing to be bound by theory, it is suspected that this occurs because the compound is located inside the granules and therefore at least partially protected from the environment, which can, for certain compounds, cause degradation by oxidation.

The dried granules have been found to be a particularly stable form of biomass. They can be stored for weeks, if not years (e.g. at room temperature), with little or no degradation or changes in its properties. This means that the compound(s) it contains can also be stably stored (or even transported). Furthermore, it can be stored at room temperature, which avoids the need to freeze, or store at particularly low temperatures, which is the case for prior art biomass materials. Clearly, such stability is advantageous as the storage conditions are considerably cheaper.

The preferred method of granulating the biomass is by extrusion. This can minimise destruction of the cells. The stability of the biomass has been found to be better with minimum disruption of the cells, in other words the process of the invention can be adapted to optimize the number of cells that remain intact. This is in contrast to many prior art extractions, where the cells are disrupted in order to isolate the compound.

The present invention also relates to a process for the isolation of one or more PUFAs from granules of biomass, the process comprising:

a) providing dried granules having a dry matter content of at least 80%, the granules having been derived from a microbal biomass comprising microorganisms that have produced a PUFA; and b) extracting or isolating the or each PUFA from the dried granules by solvent extraction.

The preferred extraction method is to employ a solvent, in which suitably the compound is soluble. The preferred extraction method is to use percolation: here the solvent can be passed over a bed of the granules. For this technique it will be appreciated that the particles should not be too small (for example they should not be milled or comminuted) otherwise one will obtain too much "dust" (or fines) which will clog the filter. Large particles are also to be avoided, but in between these two extremes one can obtain an optimal surface area, so that preferably the granules are larger than the pores of the filter. The particles are preferably highly porous to allow easy access of the solvent to the compound to be extracted.

The pretreatment of microbial biomass cake to form granular particles can significantly improve the subsequent drying process. The resulting dried granulated biomass can be particularly suitable for either immersion or percolation extraction. The particle size can be specifically adjusted for optimal drying and extraction conditions. By using biomass pretreated according to the invention, the desired compound is advantageously extracted without the need to disrupt the cells prior to extraction.

The process of the invention can be used to prepare granular particles or dried granules from almost any type of microorganism. The microorganism can be in a filamentous form, like fungi or certain bacteria, or as single cells, like yeasts, algae and bacteria. Thus, the biomass may comprise microorganisms that are yeasts, fungae, bacteria or algae. Preferred fungae are of the order Mucorales. For example, the fungus may be of the genus Mortierela, Phycomyces, Blakeslea, or Aspergillus. Preferred fungae are of the species *Mortierella alpina, Blakealea trispora* and *Aspergillue terreus.*

As far as yeasts are concerned, these are preferably of the genus Pichia, such as of the species *Pichia ciferrii.*

Bacteria can be of the qenus Propionibacterium.

If the biomass comprises an algae, this is preferably a dinoflagellate and/or belongs to the genus Crypthecodinium. Preferred algae are of the species *Crypthecodinium cohnii.*

The compound to be isolated from the microbial biomass prepared according to the invention may be located intracellularly, associated with the cell membrane or cell wall, or produced extracellularly (it may then be insoluble in water).

The compound to be isolated can be either hydrophilic or hydrophobic (e.g. lipophilic). Examples of such compounds are intracellular proteins or enzymes, lipids, secondary metabolites like vitamins (e.g. vitamin $B_{12}$), macrolide or polyene antibiotics, flavor providing substances or carotenoids. Preferably, the compound to be isolated from microbial biomass is a lipophilic compound.

The compound extracted from the biomass treated according to the invention can be of high quality since it has been subjected to little, if any, deterioration due to the mild conditions used in the treatment process. Therefore, the invention is particularly suitable for the preparation of microbial biomass from which heat- and/or oxidation-sensitive compound(s) need to be isolated.

The second aspect of the invention is suitable for preparing microbial biomass for the isolation of compounds having a high degree of unsaturation, such as lipids containing polyunsaturated fatty acids (PUPA). Preferably the PUFA is a C18, C20 or C22 ω-3 or ω-6 polyunsaturated fatty acid. For instance the compound can be docosahexaenoic acid-(DRA) (from algae or fungi, such as the dinoflagellate Cxypthecodinium or the fungus Thraustochytrium), γ-(linolenic acid-(GLA), dihomo-γ-linolenic- or arachidonic acid-(ARA) (from fungi, such as Mortierella, Pythium or Zntomophthora), or eicosapentaenoic acid-(EPA) (from algae, such as Pozphyridium or Nitzuchia). Any of these PUFAs may be isolated either on their own or, more usually, in the form of a lipid.

Additional examples of compounds which can be isolated according to the (fourth aspect of the) invention include β-carotene, such as from fungal genera e.g. from the order Mucorales, e.g. Phycomyces or Blakeslea, astaxanthin from the yeast *Phaffia rhodozyma,* tetraacetylphytosphingoeine (TA-us) from the yeast *Pichia ciferrii,* and/or vitamin B12 from propionic bacteria.

Other compounds that can be extracted include lipophilic/non polar ones such as lovastatin, cyclobporin and laidlomycin. Of these, the first two are either produced extracellularly or attached to the cell wall. Suitable solvents, therefore, include heptane, hexane, acetone, methanol and toluene, and ethanol. However, for the later two compounds, one can use isopropyl alcohol or butyl acetate for cyclosporin, and ethanol or methanol for laidlomycin. Generally speaking, hexane is suitable for soluble antibiotics, such as those produced by the organisms of the genus Streptomyces.

Other compounds include polyketides, or metabolites derived from polyketides, which includes many antibiotics. Preferred polyketides are those that do not contain nitrogen, and may be aromatic, preferably containing at least one 6 membered ring, Preferred polyketides are statins, which includes lovastatin, simvastatin, pravastatin and compactin. Other preferred compounds are HMO-CoA reductase inhibitors. These can reduce cholesterol levels in the blood.

Another class of compounds that can be extracted include steroids and sterols such as ergosterol. These are produced by yeasts and moulds.

The compounds isolated according to the process(es) compositions, of the invention are suitable for use in human or animal foods (e.g. infant formula) or other edible compositions and in cosmetics, healthcare compositions or supplements, or pharmaceutical compositions.

In the process of the invention, the microorganism of choice can first be fermented to obtain a sufficient amount of biomass for subsequent extraction of the compound. The fermentation conditions will depend on the organism used, and may be optimized for a high content of the compound in the resulting biomass.

After the fermentation process has finished, the fermentation broth, depending on the type of compound to be isolated, may be pasteurized to kill the production organism and to inactivate any undesirable enzymes. If desired, flocculation agents and/or other processing aids may be added to the broth to improve its filterability.

Suitable flocculating agents include $CaCl_2$, $Al_2(SO_4)_3$ and polar cationic polyamides. These may be present at from 0.1 to 2% by weight.

Preferably the biomass (or broth) is pasteurised. After fermentation pasteurisation may be necessary to obtain a slurry that can be processed in a hygienic way. The pasteurisation of biomass in the fermenter can have several advantages. Firstly, the production organism is not exposed to the environment. Also, unwanted enzymatic activities, influencing the quality of the target compound can be inactivated.

Depending on the species of the production organism the pasteurisation is performed at temperatures of from 60 to 100° C. The pasteurisation can be performed by heating (directly) with steam into the fermenter or by (indirect) heating using a medium via heat exchangers, either through the wall or with cooling coils or an external heat exchanger such as known plate heat exchangers or other suitable heat exchangers.

The following preferred pasteurisation conditions can be employed, especially for organisms of the genus Mortierella.

The fermentation broth (or biomass) is pasteurized to kill the microorganism and to inactivate enzyme activity. This can be about 144 hours after inoculation of the main fermenter. The biomass (or broth) is suitably pasteurized at from 50 to 95° C., preferably from 60 to 75° C., and optimally between 63 to 68° C. This can be for from 30 to 90 minutes, preferably from 50 to 75 minutes, optimally, from 55 to 65 minutes. This can be by any suitable heating means, but is preferably by direct steam injection, such as into the main fermentation vessel.

After pasteurisation the broth is allowed to cool, or is cooled down. This can take about 4 hours, suitably to about 25° C.

If two or more organisms are involved, from different biomass or fermentation broths, then each biomass (or broth) can be individually pasteurised or, after mixing, they can then be pasteurised. However, the former is preferred as different pasteurisation conditions can then be employed for the different organisms.

Usually, pasteurisation will take place in the fermenter vessel in which fermentation has occurred. However, for some organisms (such as bacteria) it is often preferred to remove the microorganisms from the vessel first, and then pasteurize (for example, before spray drying in an agglomeration granulation process).

As will have been appreciated, pasteurisation will usually kill most, if not all, of the microorganisms. Therefore, in the dried granules, at least 95%, such as at least 98%, if not 95%, of the microorganisms, have been killed (i.e. are not alive).

For some organisms (e.g. Pichia) preferably no pasteurisation is conducted.

To prevent recontamination of pasteurised biomass during subsequent processing steps conditions can be designed to reduce the risk of growth. One possibility is to acidify the broth with a suitable acid. To prevent the out-growth of many microbial species a pH range of from 3 to 4 in combination of a low process temperature is sufficient.

Also other biostatic agents like alcohols, sorbates, etc. may be used for this purpose.

For thermally stable products processing at higher temperatures (60–100° C.) may be applied.

Preferred acidifying conditions (e.g. for organisms of the genus Mortierella) are as follows.

The pH of the pasteurised broth is adjusted to from 2 to 5 to improve microbiological stability, preferably to a pH in the range of 3 to 4, and optimally a pH of about 3.5.

Acidification of the broth (before or after pasteurisation) can have additional advantages. If the compound is a polyketide, for example a statin, then acidification can result in precipitation of the compound. For many compounds, especially waster soluble ones, precipitation before further processing steps is desirable, lest the compound be lost when the broth is filtered to remove water. Therefore, before or after pasteurisation, a compound may be precipitated (such as by acidification, although any other means known to a person skilled in the art can be employed)

The pH can be adjusted by any suitable means e.g. 85% phosphoric acid, preferably diluted 55% phosphoric acid and optimally with diluted 33% phosphoric acid.

At this stage one has a broth, which may have been pasteurised. The next stage is to obtain a biomass, by separating the microorganisms from the surrounding medium.

A solid-liquid separation technique can be performed to separate the biomass from the fermentation broth. This (harvested) biomass usually has a dry matter content varying from 20 to 35%, depending on the type of microorganism. However, for extrusion (and subsequent drying) the biomass typically should have a dry matter content which ranges from 25% to 80%.

If the water content of the biomass is too high (e.g. for extrusion and/or subsequent drying), it can be dewatered and/or have its dry matter content increased. This can be achieved by a number of methods. Firstly, the biomass can be subjected to (additional) dewatering. Any dewatering method known to the skilled person can be used; the desired dry matter content can be from 25 or 30 to 80%.

Preferably, a mechanical dewatering method is used. The maximum dry matter content which can be reached by mechanical dewatering will, however, vary depending on the type of microorganism. For certain microorganisms, e.g. yeast, the dry matter content of the biomass after mechanical dewatering may not exceed a level of 35 to 40%, while the same process executed on biomass of certain lipid-rich microorganisms may result in a higher dry matter content of from 45 to 60%.

A preferred method is to use a membrane filter press (plate and frame filter press with squeezing membranes) which can combine a solid-liquid separation with mechanical dewatering and is especially suitable to obtain the desired dry matter content.

Alternatively or in addition, the desired dry matter content of the microbial biomass can be increased by the addition of consistency-increasing (or dry) agents. These consistency-increasing agents are suitably dry and, preferably, do not negatively interfere with the extraction process and/or the properties of the compound. For example, consistency-increasing agents can comprise starch and/or plant fibers such as oats or wheat bran or cellulose. Even another biomass (of a lower water content) can be used. Such substances may be added anyway, if it improves the extrudability.

Sometimes, e.g. after solid-liquid separation and/or mechanical dawatering, the biomass can form of large cakes. This may not be suitable for granulation (e.g. extrusion). To reduce the biomass to a size which may enable granulation (e.g. efficient feeding of the extruder), the biomass is suitably crumbled, kneaded and/or mixed. This crumbling and/or kneading can be achieved by (short) treatment in a high shear mixer. Optionally, the or each consistency-increasing agent may be added during this part of the process.

The then (optionally crumbled or kneaded) biomass can be subsequently subjected to the granulation process to result in the formation of granular particles. The granulation can be effected in a number of different ways.

Another method of reducing water content (or increasing dry matter content) is to use a salt (e.g. brine) wash, either of the biomass or (preferably) after separation of the biomass from the broth, such as using wash filtration.

In a preferred embodiment of the invention, the desired particle structure and size is obtained by an extrusion process. The particle characteristics, such as structure and size, can be important in order to optimise the drying and/or extraction process. During the drying step, it the particles are too small they may give problems as they can generate dust and fines, whereas too large particles do not fluidize and may give a poor drying performance. During extraction, a too small granule size may not allow the use of a percolation process, since the pressure drop over the biomass bed will be too high. Too much fines may give problems in subsequent purification steps. A too large size may impede efficient penetration of solvent during extraction. Furthermore, the particle structure should be sufficiently compact in order to prevent disintegration during drying and extraction, but the particles (dried granules) preferably have a porosity that allows (efficient) penetration of solvent during extraction.

The extrusion conditions can be adjusted by a skilled person in order to obtain granular (biomass) particles having the desired structure and size.

The extrusion conditions can be adjusted to minimize cell disruption. Minimal cell disruption can ensure optimal protection of labile, oxidation-sensitive compounds against oxidation-induced degradation. Extrusion is therefore preferably conducted at lower temperatures, without any means of heating. Preferably this is in the range of from 20 to 30° C., such as about room temperature. During extrusion the granular particles may form naturally, the "extrudate" falling away under its own weight from the die plate by the influence of gravity, thereby forming particles. If, however, the biomass is of a nature whereby after being extruded by the die plate in forms long strands like spaghetti, then the spaghetti can be cut to give particles of a desired size.

The temperature of the biomass has been found to influence the nature of the granular particles produced on extrusion. Preferably the biomass has a temperature of from 6 to 15° C. before extrusion. However, while in the extruder the temperature of the biomass can rise to be from 10 to 60° C., although preferably this is from 15 to 30° C. The temperature rise will depend upon the pressure exerted on the biomass, and its dry matter content.

During extrusion the biomass is usually forced through a barrel towards a die plate, often by a screw. This barrel is preferably not heated. In fact, it is advantageous that it is cooled. Suitably, the temperature of the coolant (e.g. an aqueous solution such as water) is from 1 to 4° C., such as about 2° C.

Generally speaking, extrusion does not change the water content. This is why in stage (b), the dry matter content is the same as in stage (a). However, as will be appreciated, other granulation techniques (such as those described later) do change the water content, and can decrease it (in other words, increase the dry matter content). For a biomass that contains a fungus, for example, of the order Mucorales (in particular one producing a PUFA) the dry matter content of the biomass in (a), which will usually be the same as in the granular particles produced on granulation (in this case extrusion) is suitably between 35 and 60%, preferably from 50 to 60%. After drying, the dry granules preferably have a dry matter content of at 10 least 90%, such as at least 95%.

The preferred granulation technique is to use an extruder. A good overview of extruders is by W. Pietsch ("Size Enlargement by Agglomeration": Wiley & Sons 1991, page 385). The machine maybe a batch or continuous extruder. For continuous extruders there may be mentioned simple single screw extruders (both axial and radial transporting). Also there are twin screw extruders either co-or counter rotating. The to be extruded biomass is transported, partly compacted and pressed through a perforated (die) plate. Another group of extruders include pelletising machines. Here a cylindric pressing tool rolls over a layer of material deposited on a perforated plate.

If the granules are obtained by extrusion, then the biomass needs to be in an extrudable form. The water content can be adjusted, if necessary, depending on the condition of the biomass, the microorganisms employed, and the extrusion conditions. Water can either be removed, or the dry matter content increased by means of addition of solids, for example starch. The biomass can in this way be adjusted to the correct consistency, which is usually that of a paste.

Although the granules can be used for extraction of the compound, they do in addition represent a stable form of the biomass that can be stored. The granules can have other uses: for example, they may be used in the preparation of an infant formula, where the biomass contains one or more polyunsaturated fatty acids (PUFAS).

The present invention also envisages other granulation methods which enable the formation of (granular) particles. For instance, a multistage drying process can comprise a combination of spray-drying and a fluidized bed and can also yield granular particles.

Other types of granulation techniques can be employed. Generally granulation is the action of obtaining solids in a granular form either by size enlargement or size reduction. In general size enlargement is employed. A good overview of the type of granulation processes available is described in W. Pietsch, "Size Enlargement by Agglomeration" (Wiley & Sons, 1991, as above). Within this there are many different techniques available for granulation and this includes several agglomeration methods, which will be described. Here agglomeration results in small particles adhering to each other (agglomerating) to form larger particles (in this case the granular ones). Therefore, if a first technique results in the particles being too small an agglomerisation technique can then be employed to give bigger (granular) particles.

Tumble agglomeration is usually achieved using a tumbling, and/or rotating drum or cone drier with a powder having adhesive properties (so that the particles stick together). In some cases an extra added binder can be mixed. By this mechanism spherical particles can be formed.

Pressure agglomeration is usually characterised by high forces acting on a mass of a particulate matter. In general this process is performed with fine powders or with 'plastic' (non-elastic) materials. This process is normally used for powdered materials. (However it is also used in dried yeast production for doughs of a certain consistency). The shaped particles may be dried to suitable dry matter content for optimal storage. Pressure agglomeration can be accomplished by a piston, roller, isostatic and/or extruder presses. A good description of this type of equipment is given in the Pietsch book mentioned above.

Extrusion presses usually make use of wall friction, causing resistance to the flow of the plastic material through bores or open ended dies. Particularly in screw extruders extensive mixing takes place and high shear forces are applied.

In general materials with low melting or plastification temperatures can be directly agglomerated.

Other agglomeration techniques are possible. For example, spray drying in combination with a fluid bed agglomerator. Initially the biomass can be dried by atomization through a nozzle or using a rotary wheel in a spray dryer. Fine particles are recycled to the spraying section. The resulting sticky powder is further agglomerated in a fluid bed section. In some cases rewetting of the powder can improve the agglomeration process. This described technique in known as multi-stage drying.

To describe multi-stage drying in greater detail, the biomass is first spray dried. This can give a fine powder. The temperature of spray drying (air inlet temperature) is usually from 160° C. to 260° C. and/or the air outlet temperature Is from 75 to 90° C. Here the biomass is sprayed by a fast rotating disk or a nozzle which generates small particles. The particles can then fall, under gravity, towards the bottom of a spray drying tower. Here, a fluid bed may be provided, which can use hot air to effect drying (suitably at 90 to 95° C.). Here, agglomeration can take place, and the particles can stick together. Following this, the agglomerated (granular) particles are subjected to drying, for example on a belt drying bed or on a sub-fluidised bed. At the start of the process, a biomass can have a dry matter content of below 30%. After spray drying, this can increase to from 75 to 90%, and after agglomerisation can be from 90 to 95%. After drying, this can increase to at least 95%.

Another technique is to use a fluidised bed agglomerator. Here, powder can be fluidised in a gas flow. In the particle bed a fluid is sprayed with water that wets the powder and enhances the agglomeration.

In general the described agglomeration processes are for dry powders that can be plazticized. An exception is the drying on a multi-stage dryer. This combination of spray drying in combination with a fluid bed after dryer is suited for the agglomeration of many different types of biomass. However the process is not always suitable for thermo-labile products or products susceptible to oxidation by (hot) air. A good way of producing a granulated dry biomass is the extrusion of a mechanically dewatered filtercake followed by a suitable drying step like fluid bed or sub-fluidised bed drying.

Another way of agglomeration of (dried) biomass can be performed by the rewetting of (spray) dried product followed by an extrusion step and re-drying in e.g a fluid bed dryer. Powders, with a low melting point or a low plasticising temperature (or in case of certain dried biomasses with a high amount of intracellular oil, that partially melts due to the forces in the extruder) can be extruded. Suitable pellets form in the die plate.

As in (c) above, the (extruded or otherwise) granulated is biomass can be dried, suitably under conditions that allow the particles to remain intact. The particle structure and size of the biomass after the granulation process is thought to enable the efficient drying of the biomass. The drying can be performed using various dryers, e.g. a belt dryer, a vacuum or a vacuum belt dryer, a fluidized or a subfluidized bed dryer. The skilled person can choose between a batch or a continuous process.

The use of a fluidized or subfluidized bed dryer is especially preferred in the process of the invention. Drying can occur in air or under nitrogen. With fluidized and subfluidized bed drying, the temperature in the bed can be adjusted to preset values. These values can range widely, for example from 35° to 120° C., such as 50 to 90° C., optionally from 60 to 80° C. If a labile compound needs to be isolated from the biomass, the temperature of the drying process can easily be adjusted to the lower ranges, to diminish the risk of oxidation or degradation.

Alternatively or in addition a vacuum drying process can be employed, e.g. at from 1 to 2 hours.

Several advantages may flow from the drying step. First, drying of the biomass particles (to form granules) can result in an intermediate material which may be stably stored for a prolonged time period. Here a (relatively) high dry matter content of the biomass may prevent degradation of the compound to be isolated from the biomass. In this way, the dried granules can be considered as a stable formulation of the compound present within or associated with the biomass.

For instance, the granules can function as a carrier for an enzyme, whereby the enzyme is immobilized within the granules by mixing an appropriate amount of a cross-linking agent, e.g. glutaraldehyde, into the biomass before extrusion.

In addition, the dried granules prepared according to the invention can be advantageously used as it is, for instance as a food or feed composition or additive.

The particles and/or granules (e.g. produced by extrusion) can have the following properties.

The granules can have the shape of chocolate confetti. The diameter of the (extruded) granules can vary from 0.1 to 12 mm, such as from 0.3 to 10 mm. More preferred is from 1.5 mm to 6 mm and optimally (for extraction when dried) the diameter is from 2 to 3 mm. The length of the granules can be about 2 to 5 or 6 times the diameter. They can then be easily handled in packing and used with commercially available extractors (to guarantee the permeability of the bed). Usually most, if not substantially all, the granules will have the same size, indeed, one can obtain highly uniform or homogeneous granules where at least 80%, such as at least 90%, of all the granules have a particular property within the range specified.

The composition of the second aspect (the granules) are preferably free-flowing. They maybe roughly cylindrical in shape. This can be achieved by using extrusion. The particles can then be of a diameter that is approximately the same (although it may be slightly larger) than the holes of the die plate used for extrusion. During this process, particles may form automatically on exiting the die plate. In that event, the length of the particles will be variable. However, particle length can be influenced for example, if one uses a cutting means, for example a knife (e.g. one or more rotating blades adjacent to the die plate) when most (if not all) of the particles will have substantially the same length. Preferred lengths of such particles are at least 2 mm, such as at least 3 mm. Suitably the granules are of a size and water content that allows them to be "epoured" which allows them to be stored and transported more easily. Although, generally speaking, most particles will be elongate in nature, some may be approximately spherical. The preferred lipid content of the granules is preferably from 30 to 50% by weight.

The bulk density of the granules will usually be from 400 to 1100 $kg/m^3$.

As has been discussed, the granules are preferably porous, in order to allow access of the solvent to the compound to be extracted. Preferably, the granules have hollow channels, and these may extend towards, and into, the center of the granules. The number of channels may be such that from 40 to 60% such as from 45 to 55%, optimally about 50%, by volume of the granule is hollow (air). As far as the channels are concerned, they may be in length 10 to 20 times that of their average diameter. The granules will, generally speaking, be homogeneous in their composition, in that the outside of the granule, will in essence, be the same material as that in the center. This is in contrast to prior art yeast compositions which may have a relatively solid outside but yet relatively airy core.

The granules can be stably stored at a temperature optimal for the compound to be eventually extracted.

The preferred dry matter content of the dried granules is more than 80%, more preferably at least 85%, mostly preferably at least 90% and optimally in the range of from 93 to 97%. If a water miscible solvent is to be used for extraction granules with lower dry matter contents can be used.

The (dried) granules are thus usually porous so solvents used in extraction can gain easy access to the (inside of) the granules. Thus, during extrusion and drying the amount of dust can be minimised (which increases yield) and can avoid an additional filtration of the (solvent) extract prior to evaporation of the extract.

The porosity of the granules is dependent on the (water or) dry matter content of granular particles. Often the water in the granular particles will be evaporated on drying to leave a (hollow) pore. The porosity of the dried granules is preferably from 15 to 50%, such as from 20 to 40%, optimally from 25 to 35%.

Preferably, most (if not substantially all) of the cells in the granules are intact (that is to say not ruptured). The granules especially from a fungal biomass, can be wholly biomass particles which have a diameter from 0.3 to 10 mm, preferably a diameter of from 0.7 to 5 mm, optionally from 1 to 3 mm. Commonly, the particles will automatically form at the desired length. Otherwise, the particles may be cut to the desired length. If granulation was by extrusion, then the holes in the die plate of the extruder can generally correspond to the diameters of the granules.

Optionally, antioxidants may be added prior to or during the granulation process. These can include tocopherol and ascorbyl palmitate, e.g. present at up to 0.1% (by weight).

The invention may thus provide a biomass material with characteristics that may enable a cost-effective and efficient extraction of compounds. The compound(s) present can then be purified, isolated or (preferably) extracted. The process of the invention can enable the use of a percolation extraction process. The advantage allowed by this extraction process seem to be due to the structure and size as well as a high dry matter content. A dry extrudate requires a reduced amount of solvent for the extraction of the valuable compound therefrom. In addition, the process of desolventizing toasting, i.e. the release of used solvent from the biomass, can be performed better and more efficient with biomass in the form of an extrudate.

The extrudate residue obtained after the process of desolventizing toasting can advantageously be used as a feed component.

A dry matter content of the extrudate exceeding 90 to 95% may enable stable storage of the extrudate, whereas a dry matter content above 85% already can give a significant advantage in the subsequent extraction process.

Extraction is preferably conducted using a solvent. The solvent employed will depend upon the compound to be extracted, but in particular one can mention $C_{1-10}$ alkyl esters (e.g. ethyl or butyl acetate), toluene, $C_{1-3}$ alcohols (e.g. methanol, propanol) and $C_{3-6}$ alkanea (e.g. hexane) and/or a supercritical fluid (e.g. liquid $CO_2$ or supercritical propane). In prior art techniques, the solvent has been employed directly on the microorganism in the broth. However, by performing extraction on the granules, one can significantly reduce the amount of solvent required. In some of the applicant's experiments, 20 to 30 times less solvent was needed in order to perform the extraction. Not only does this result in a significant economic saving, because less solvent but is used, it also minimises emission problems. By using granules the surface area available to the solvent can be particularly high and therefore one can obtain good yields.

If the compound to be extracted is hydrophobic, then an apolar solvent is preferably used. For hydrophilic compounds, a polar solvent (such as a alcohol) is suitably employed.

Extraction can be effected using a variety of techniques. The preferred method is percolation extraction, using a filter. Here, a column can be filled with the dried granules. The solvent (hexane) is then added to cover the granules. Although the solvent can be passed once through the column and over the dried granules, preferably it is recirculated (either as a closed or open system). Suitably the solvent is recirculated for three to seven times, such as about five times, suitably for a time period of from half an hour to one and a half hours such as about one hour. FIG. 3 shows a suitable percolation extraction apparatus. The solvent is held in the vessel before addition to the percolation extractor containing the dried granules. The solvent is circulated by means of the pump. The polish filter is intended to remove fines.

Other percolation extractors can be employed. These may be of a counter current or cross-current design. In the former, the dried granules can be held in a rotating cylinder (such as a carousel) split into various sectors. The solvent is passed through the granules in one sector in one direction, and then passed through (preferably in the same direction) granules in another (such as a neighboring) sector. These machines are often referred to as carousel extractors and are available from Kripp, Germany.

In another technique, the granules can be placed on, for example, a moving (e.g. porous) belt or conveyer which is moving in a substantially opposite direction to the solvent. This can mean that fresh granules are extracted with solvent that has already passed through other granules, and that fresh solvent is applied to granules that have previously been subjected to extraction with the solvent. This arrangement can maximise efficiency.

In a cross-current technique separate batches of the granules are subjected to extraction with portions of fresh solvent.

The process of the invention can also be used to obtain a mixture of two or more compounds from different microorganisms by preparing granular particles or granules from a mixture of two or more microorganisms. This mixture of microorganisms can be obtained by mixing the fermentation broths of two or more different microorganisms directly after has finished or by combining the biomass from two or more microorganisms immediately prior to the granulation (e.g. extrusion process). It is also possible to mix two or more different microbial extrudates prior to the extraction process.

A preferred process according to the present invention may thus be as follows:
 a) fermenting one or more microorganisms in a suitable medium, under conditions that allow the microorganism to produce the desired compound, which can result in a broth (of the microorganisms in the surrounding medium);
 b) if necessary, precipitating or solidifying the compound, such as by acidification;
 c) separating the microorganisms from the medium in the broth, which may be achieved by solid/liquid separation, such as by filtration, in order to obtain a biomass;
 d) pasteurisation, either of the broth resulting from (a) or of the biomass resulting from (c);

e) if necessary, increasing the dry matter content of the biomass, for example by adding dry matter or substances, or by decreasing the water content, for example by a dewatering or drying technique;
f) crumbling and/or kneading the resulting biomass (and, optionally, increasing the dry matter content by adding one or more dry substances);
g) granulating the biomass to give granular particles, such as by extrusion;
h) drying the granular particles to give dried granules; and
i) extracting one or more of the compounds, such as by using a suitable solvent.

The compounds isolated according to the invention can be of high quality and may be suitable for use in human or animal nutrition. Especially polyunsaturated fatty acid (PUFA)-containing lipids isolated according to the invention are suitable for nutritional purposes, in particular for the incorporation in infant formula.

The invention will now be described, by way of example, with regard to the following Examples which are provided by way of illustration. They are accompanied by the following drawings in which.

EXAMPLES 1 TO 6

Figure 1:
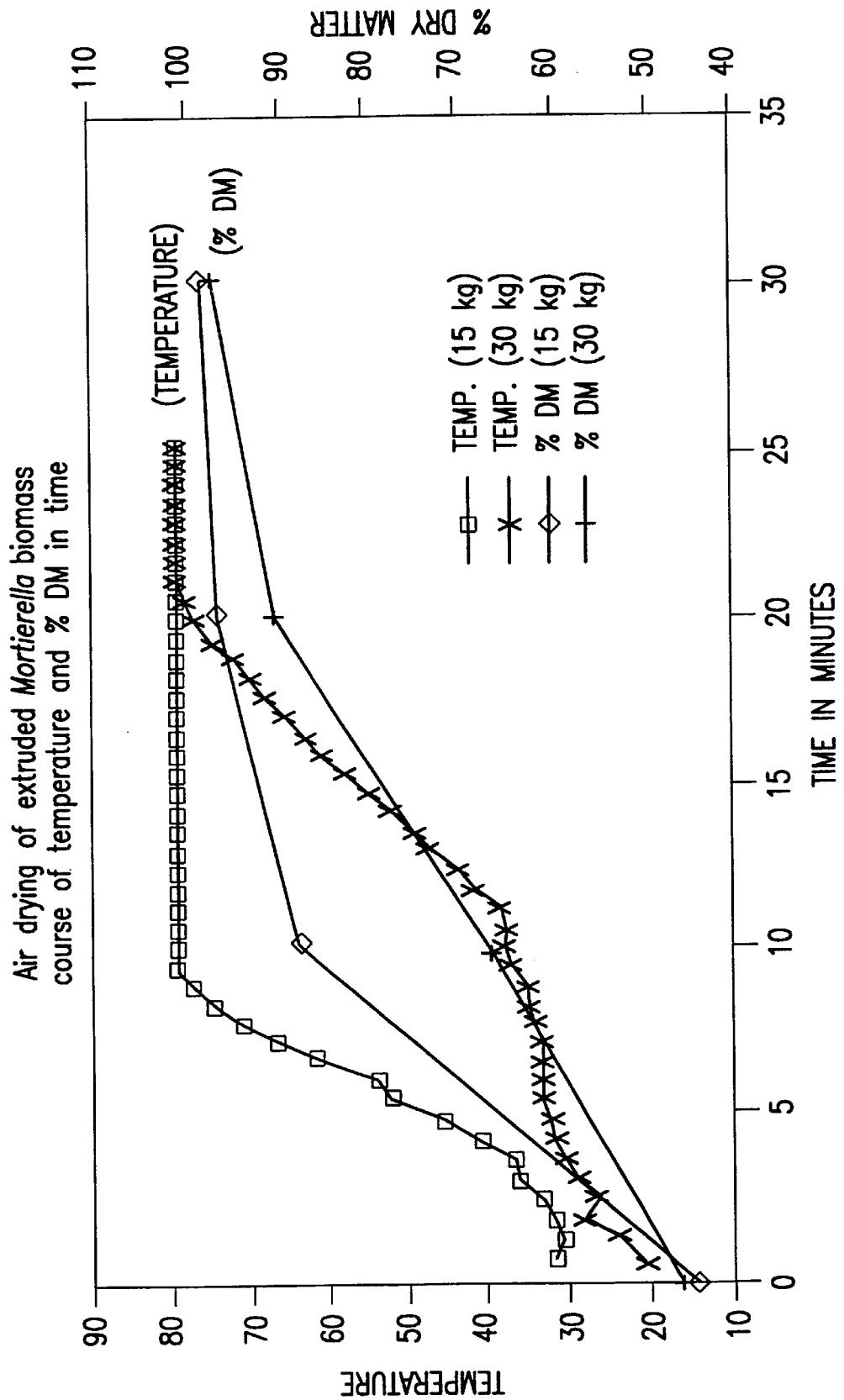
FIG. 1 is a graph of temperature and dry matter (%) against time showing the drying behavior of different amounts of extruded biomass at different temperatures.

Processing of Mortierella Fermentation Broth 160 l of a fermentation broth of *Mortierella alpina*, previously pasteurised (68° C. for 1 hour) (palletized growth) was filtered in a standard Dieffenbach plate and frame filter press (cloth type: nycot 2794). The broth was filtered with a maximum applied pressure of 1.0 bar. Within 20 minutes 160 l broth was filtered over a total filter area of 4.35 m², which resulted in an average flow of about 110 l/m²h. The filter cake was washed with about 3 cake volumes (≈150 l) of process water.

About 30 kg of wet cake was recovered with a dry matter content of about 25%. Three types of drying procedures were employed.

Vacuum drying:
10 kg of filtercake was dried under vacuum at 35° C. in a vacuum (about 50 mbar) tray dryer (about 1 m² drying surface) during 24 hours resulting in about 2.5 kg of dried biomass with a dry matter content of about 94%. The dried biomass consisted of crumbled biomass and some big lumps. Vacuum drying was time consuming probably due to the big lumps.

Ventilation tray dryer:
10 kg of filtercake was dried under nitrogen during 24 hours at 35° C. in a ventilation tray dryer (about 1 m² drying surface). In total about 2.5 kg of dried biomass was recovered with a dry matter content of about 93%. The dried biomass consist of crumbled biomass and some big lumps. Ventilation tray drying was time consuming probably due to the big lumps.

Fluid bed dryer:
5 kg of filtercake was dried in a labscale fluid bed dryer of AEROMATIC (type MP-1) at an inlet air temperature of about 200° C. The outlet temperature was about 40° C. In about 45 minutes the wet biomass was dried resulting in about 1 kg of dried biomass with a dry matter content of about 81%.

The dried material recovered by this last method was used for extraction of oil by means of hexane at six different temperatures (hence Examples 1 to 6). 150 g of the dried biomass was subjected to extraction with 1500 ml of hexane (heated to reflux) under nitrogen blanketing for 90 minutes. The cell mass was filtered off and the solvent in the resulting micella was evaporated in a rotavapor under vacuum. This resulted in a crude PUPA oil. The results are shown in Table 1. Extraction at room temperature gave lower yields; better yields were obtained at elevated temperatures.

TABLE 1

Extraction of oil from biomass.

| Experiment number | Biomass/hexane ratio | Temperature in ° C. | Extraction time in minutes | g oil per 100 g dried biomass |
|---|---|---|---|---|
| 1 | 300 | 80 | 30 | 19.2 |
| 2 | 100 | 23 | 30 | 16.4 |
| 3 | 150 | 45 | 60 | 22.6 |
| 4 | 200 | 23 | 120 | 17.1 |
| 5 | 200 | 23 | 30 | 11.8 |
| 6 | 100 | 23 | 120 | 13.5 |

The triglyceride rich oil was a light yellow oil, and contained some solid material.

EXAMPLE 7 AND COMPARATIVE EXAMPLE 8

Processing of Mortierella Fermentation Broth 500 l of broth (previously pasteurised as described in the previous Example) was filtered in a membrane filter press (SCHULE) at a pressure difference of about 0.5 bar. The filtercake was washed with 10 cake volumes of process water and afterwards squeezed during 30 minutes at 5.5 bar. The resulting cake had a dry matter content of about 46%. The cake recovered in this way was extruded in a pilot extruder (ODEKERKE, diameter barrel of 50 mm, barrel profiled). The die-plate had 10 holes with a diameter of 1.6 mm each. In total 19 kg of filtercake was extruded in about 45 minutes.

The extrudate recovered in this way was dried in pilot plant fluid bed dryer (T4 AEROMATIC 0.26 m² drying surface). Within about 45 minutes the extrudate was dried at 65° C., resulting in a dry matter content of about 85% (Example 7).

During the same experiment some filtercake was not extruded (Comparative Example 8) and dried in a vacuum tray drier at 40° C. The drying was very time consuming due to the big lumps.

Both materials were subjected to extraction using hexane. The following characteristics of the materials found:

Dried extrudate: mainly pellets
(Example 7) extraction process reasonably easy
Vacuum dried biomass: pellets and lumps, much fines
(comparative Example 8) extraction process difficult; poor filtration properties

EXAMPLES 9 AND 10

Extrusion Experiments Using the Same Broth from Example 7 were Performed Using the Following Extruders LALESSE (Arnhem, Netherlands):

In Example 9 a LALESSE single screw universal extruder was used. This type of extruder is normally used in the production of food snacks, Ground maize(dry matter content of about 95%) was first fed as a test to the extruder and under pressure and heat the maize was extruded; once out of the die the extrudate expanded.

The barrel of this type of extruder was a profiled barrel in order to transport the maize processed. The type of screw used in extrusion is dependent upon the type of material processed. The screw was a universal transport screw or a compression screw with a diameter of 48 mm. The LALESSE machine is a 7.5 Kw pilot machine (drive on capacity). The total power requirement of the machine is 12.1 Kw. The barrel of the extruder could be heated or cooled. Dieplates with 1 up to 4 holes with diameters of 1.8, 2.0 and 2.2 mm used during extrusion of biomass.

The capacity for extending the Mortierella biomass (cooled barrel) was about 40 kg/h. In the extrusion is the length/diameter (L/D) ratio of the hole in the die-plate was varied.

ALMEX (Zutphen, Netherlands):

In Example 10, using the Mortierella biomass of Example 7, an expander extruder from the company ALMEX was used. This type of extruder is used in the production of pet-food. It had a smooth barrel with pins that enabled transport of the biomass. These pins have the same function as the profiles in the barrel of the LALESSE extruder. The screw of the expander extruder was a modular screw.

Technical data: ALMEX Contivar 150 L/D of 10 (ratio of the length of the screw and the diameter of the screw) Max. screw speed of 180 rpm 22 Kw (drive on capacity) Diameter screw of 150 mm Cooling with tapwater Die plates: 3 rings of holes with each hole a diameter of 1.8 mm The biomass was raised to about 25° C. in temperature during processing. The capacity of the machine was about 250 kg of Mortierella extrudate per hour.

COMPARATIVE EXAMPLE 11

Comparison of Solid/liquid Separation Performed with Different Methods

Decanter:

350 l of broth obtained from a fermentation of *Mortierella alpina* was decanted in the 'FLOTTWEG' decanter (type Z 23-3/441). The speed was set at about 4000 rpm. The differential speed range was varied during operation from 7.5-20 rpm.

The feed was set on 400 l/h. The biomass was not washed. In total 350 l broth was decanted. The temperature of the feed was 8° C. and of the supernatant 15° C. The dry matter content of the recovered biomass was about 25%.

Decanter+vacuum drum filter:

20 kg of the biomass from the decanter experiment above with a dry matter content of 25% was suspended in 500 l process water in which 10 kg NaCl was dissolved. The resulting slurry was filtered on a vacuum drum filter with belt discharge (PAXMAN, cloth type: 865.912 K/5 polyprop) without further washing. The speed of the drum was set on 1 rpm and the pressure difference on a maximum of 600 mbar. In total 400 l was filtered within 15 minutes. The net filtering surface was about 0.3 m$^2$, which resulted in an average flow of 5000 l/m$^2$h (filtering surface). The filtration rate was very well but the 'cake building' was rather bad. The dry matter content of the recovered filtered biomass was about 35%.

Plate and frame filter press:

500 l of broth was filtered in a plate and frame filter press (standard R&S, cloth type: nycot 2794). The broth was filtered with a pressure difference of 0.3 bar. Within 35 minutes 500 l broth was filtered over a total filter area of 5 m$^2$, which resulted in an average flow of ±175 l/m$^2$h. The filter cake was washed in 30 minutes with about 2.5 cake volumes of process water which resulted in an average flow of 400 l/m$^2$h.

The cake was blown dry by air for 30 minutes, which resulted in a dry matter content of the recovered biomass of about 25%.

Membrane filter press:

700 l of broth was filtered in a membrane filter press (SCHULE, cloth type: propex 46K2). The broth was filtered with a pressure difference of 0.3 bar. Within 30 minutes 700 l broth was filtered over a total filter area of 6.8 m$^2$ which resulted in an average flow of about 205 l/m$^2$h.

The filter cake was washed in 7 minutes with 3 cake volumes (≈300 l) of process water, which resulted in an average flow of 375 l/m$^2$h.

The advantage of a membrane filter press over a plate and frame press is that the cake after filtration can be squeezed at high pressure, so the dry matter content of the cake will increase. The cake was squeezed at 5.5 bar during 30 minutes which resulted in a dry matter content of the recovered biomass of about 45%.

In another experiment 1100 l of broth was filtered in a membrane filter press (SCHULE, cloth type: propex 46K2). The broth was filtered with a pressure difference of 0.3 bar. Within 45 minutes 1100 l broth was filtered over a total filter area of 12.3 m$^2$ which resulted in an average flow of about 120 l/m$^2$h. The filter cake was washed in 18 minutes with 3 cake volumes (≈600 l) of a 1% NaCl solution, which resulted in an average flow of 162 l/m$^2$h.

The cake was squeezed at 6 bar during 30 minutes, which resulted in a dry matter content of the recovered filtercake of about 55%.

Both squeezing as well as washing of the cake with a 1% salt solution had a significant effect on the dry matter content of the filtercake.

EXAMPLE 12

Extrusion of Biomass with Different Dry Matter Contents

Extrusion was performed with biomass with different dry matter contents, which were obtained by the method presented in Example 7 (see Table 2). Extrusion was performed using a single screw extruder with a profiled barrel and a universal screw. The dieplates applied in extrusion had a different number of holes and the diameters of the holes were in the range of 2 mm.

The diameter of the particles obtained after extrusion was about 2 mm.

The performance and extrudate quality is depending on the percentage dry matter of the biomass used for extrusion. Although a 25% dry matter gave the poorest results, for other microorganisms such a low dry matter content can be acceptable.

TABLE 2

Results of extrusion experiments with biomass with different dry matter contents.

| % Dry matter | Performance of extrusion | Quality of extrudate |
| --- | --- | --- |
| 25 | bad | very sticky material |
| 35 | good | sticky material |
| 45 | very good | non sticky extrudate |
| 55 | very good | loose extrudate |

EXAMPLES 13 AND 14 AND COMPARATIVE EXAMPLE 15

Drying of Conventional and Extruded Biomass
Vacuum Drying

Conventionally recovered biomass (Comparative Example 15, not extruded) was dried in a vacuum tray dryer but took about 50 hours at 40° C. The drying was very slow because of lumps. The dry matter content of in this way dried biomass was about 92.5%.

For comparison about 20 g of extrudate (from Example 11, $\emptyset_{particle}$ of 2 mm) with a dry matter content of 55% was dried on labscale in a rotavapor. The temperature of the waterbath was 68° C. and the applied pressure 40 mbar. The performance of the drying was reasonable, except that the dried biomass stuck to the wall and sweated a little oil. The dry matter content after drying was 92.3%.

Fluidized bed drying:

In Example 13 drying was performed with biomass at different temperatures. Where no pretreatment of the biomass has occurred, big lumps of biomass did not become completely dry. In this case the dried biomass was very inhomogeneous considering the particle size.

If the biomass was pretreated before drying by means of extrusion, the performance of drying substantially improved. In this case the particle size of the dried biomass was more uniform.

The conclusion of these results is that fluidized bed drying can be performed with different forms of isolated biomass, but that drying will be improved using an extrudate.

In another experiment (Example 14), drying of different quantities (15 and 30 kg) extrudate was performed in a fluidized bed dryer with air (8000 Nm$^3$/m$^2$h). During drying samples were taken and the dry matter content calculated. In FIG. 1 the relationship between temperature and dry matter content of the (two) different quantities is shown.

The bed temperature was set on 80° C. The diameter of the extruded biomass was 1.3 mm. The dry matter content of the extruded biomass after drying was about 96%.

EXAMPLE 16

Extraction of Lipid from Dried Extrudate of
*Mortierella alpina*

Stirred extraction of dried extrudate at different temperatures:

Samples of 100 g of dried extrudate with respectively 93.4 and 97.8% dry matter were extracted during 3 hours with 500 ml hexane or 500 ml propanol-2, at temperatures of 20°, 35° and 50° C. for hexane and 20°, 40° and 70° C. for propanol-2. The slurry was stirred by means of a two blade stirrer in a 'four-necked' round bottom flask and heated by means of a heating mantle. Eventually evaporated hexane or propanol-2 was recycled by means of a reflux cooler.

During the extraction, every 30 minutes a 15 ml sample of the supernatant was taken from the flask after the stirrer was stopped and the particles had settled. 1 ml of the samples was pipetted into preweighed 2 ml eppendorf tubes. After overnight drying under vacuum at 40° C. the eppendorf tubes were weighed and total oil was calculated.

Figure 2:
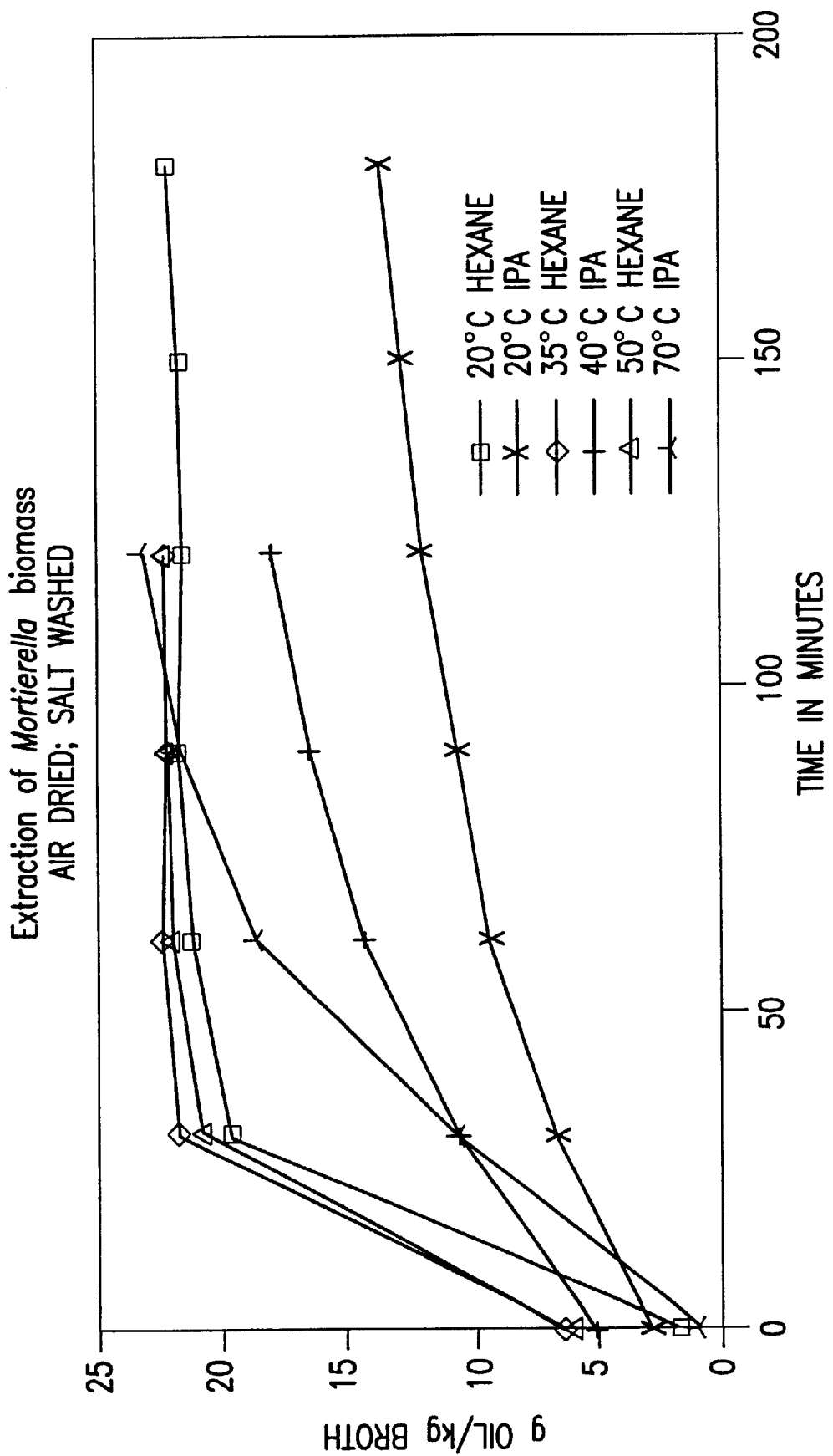
FIG. 2 is a graph of oil yield against temperature showing from extruded biomasses at different temperatures.

The results of the experiments are shown in FIG. 2.

Conclusion for hexane extraction:
  the temperature had no effect on the total amount of lipid that can be extracted, i.e. a relatively low extraction temperature gives a good yield of lipid,
  the temperature had only a small effect on the time in which the total amount of lipid can be extracted,
  the total amount of lipid was extracted within 30 minutes from the biomass, with 5 volumes of hexane at a temperature above 20° C.

Conclusion for propanol-2 extraction:
  the temperature had a significant effect on total amount of lipid that can be extracted,
  the temperature had a significant effect on the time in which the total amount of lipid can be extracted,
  the total amount of lipid was extracted within 2 hours from the biomass with 5 volumes of propanol-2 at 73° C.

The composition of the oil depended on the solvent used in extraction (see Table 3). The more polar the extraction solvent the more phospholipids were extracted. The polarity of the solvent can be chosen to optimise the composition of the oil.

TABLE 3

Extraction of dried Mortierella biomass at room temperature using two different solvents.

| Substance | hexane oil | propanol-2 oil |
| --- | --- | --- |
| Tri-glycerides | 93% | 85% |
| di-glycerides | 2% | 2% |
| mono-glycerides | 2% | 2% |
| sterols | 3% | 3% |
| phospholipids | 2% | 6.5% |

On a larger scale problems were observed with the filtration of the micella, due to disintegration of the extrudate into small particles due to the high stirrer speed during the extraction process.

These problems were avoided using percolation extraction instead of stirred extraction.

Figure 3:
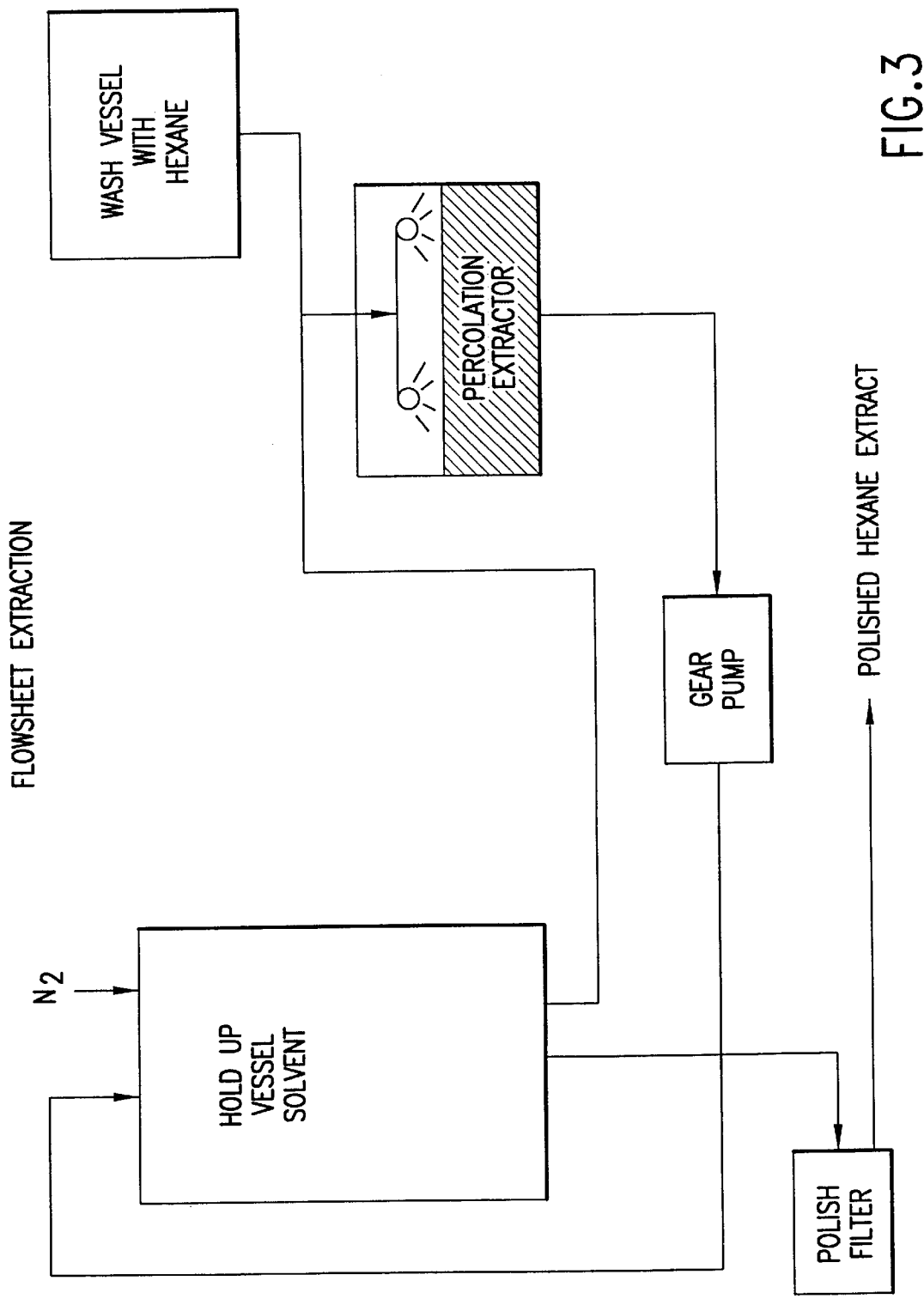
FIG. 3 is a flow diagram of a (known) percolation extraction process.

Percolation extraction of dried extrudate with hexane:

Several percolation extractions were performed on pilot scale (see FIG. 3 for a diagram of the process). About 40-45 kg of dried extruded biomass was extracted with hexane (initial hexane/biomass ratio of 4.4 l/kg) at 20° C. The flow of the gear pump was set on 1.5 m$^3$/h. There was a small nitrogen purge on holdup vessel of about 0.1 bar.

Figure 4:
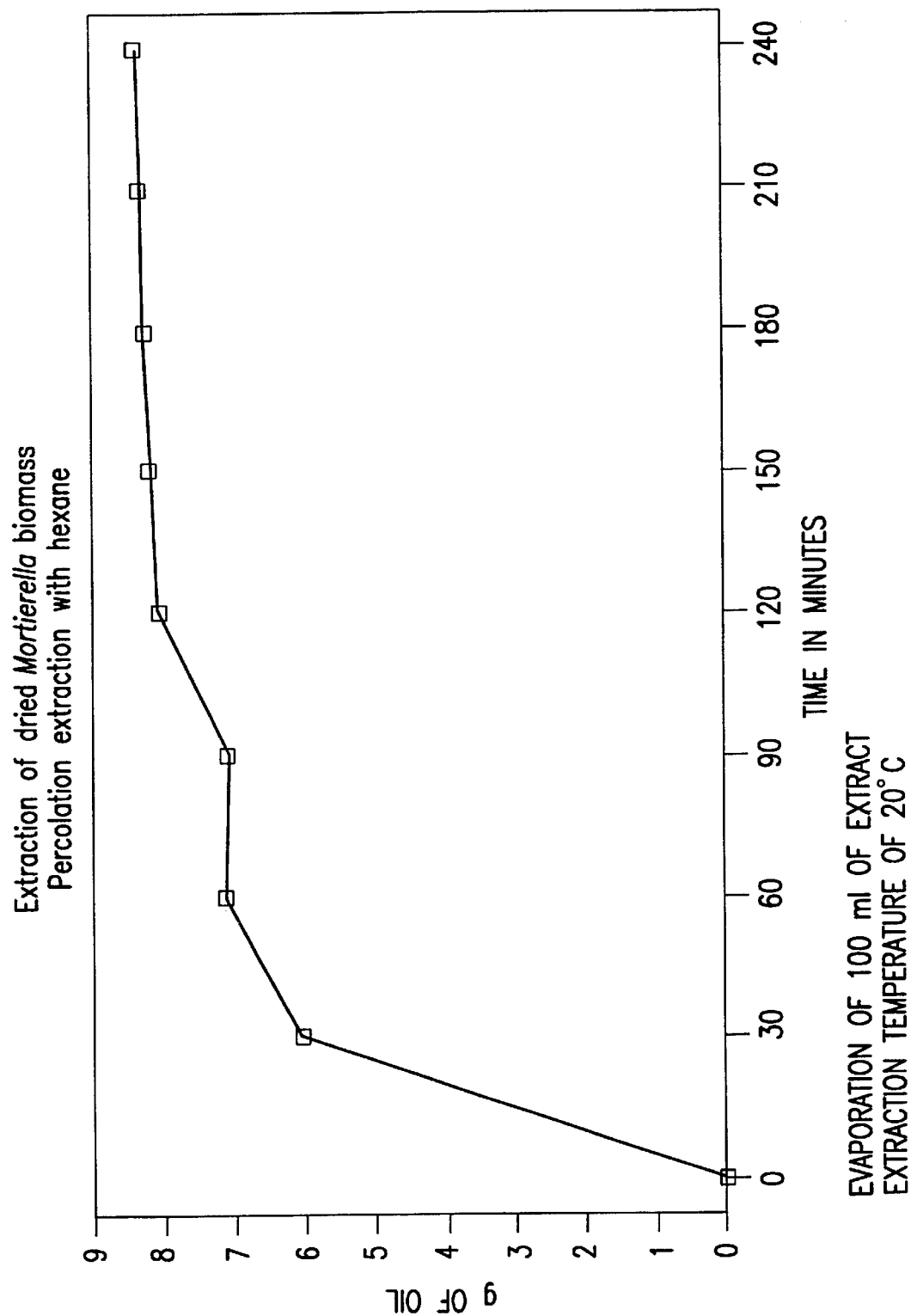
FIG. 4 is a graph of oil yield against time showing the relation between the amount of oil extracted and its time of extraction.

The extraction was performed during 4 hours (temperature increase during extraction from 18 to 25° C.). Each 30 minutes samples were taken from the micella. Of each sample, 100 ml was evaporated at labscale in a rotavapor (T$_{waterbath}$ was 64° C.) during 20 minutes under vacuum (about 50 mbar). The amount of oil was estimated. The results are presented in FIG. 4. It can be noticed that after 2 hours an 'equilibrium' was reached. Afterwards, the extracted biomass was washed with about 0.6 bed volumes of hexane. During the extraction the bed height did not change.

The micella were polish filtered prior to evaporation. During the extraction we noticed that the micella became more and more clear, due to depth-filtration over the bed of particles.

EXAMPLE 17 AND COMPARATIVE EXAMPLE 18

Recovery of β-carotene oil from *Blakeslea trigrora*

10 l of a fermentation broth of the fungus *Blakeslea trispora*, previously pasteurised (75° C. for 15 minutes), was harvested using laboratory filtration equipment. To improve the filterability of the broth $CaCl_2$ was added (end concentration of 5 g/l). In this way recovered biomass was mechanically dewatered (squeezed) at labscale up to a 45% dry matter content using a typical fruit press (citrus press, FAFICO D.G.M)). The cake recovered in this way was extruded by means of a syringe of stainless steel equipped with a die-plate with 4 holes of 1.8 mm diameter each. The resulting extrudate was dried in a labscale fluid bed dryer ($T_{air}$=40° C., drying time of 90 minutes, airflow of 150 $Nm^2$/h, ARROMATIC MP-1). The dry matter content of the biomass dried in this way was about 95%

A sample of about 50 g of dried extrudate was extracted using percolation extraction with ethyl acetate (initial volume/biomass ratio of 30 l/kg). After 2 hours of extraction at 50° C. the extract was harvested by means of vacuum filtration. The biomass was washed with 1 bed volume of ethyl acetate. The extract recovered in this way was washed twice with demineralised water (extract/water ratio of 5 v/v) prior evaporation. The ethyl acetate was evaporated at 50° C. ($T_{waterbath}$) until a concentration of 8 g β-carotene/l was reached.

β-carotene crystals were recovered from the concentrate by means of controlled crystallisation and subsequent filtration.

The same experiment was performed with biomass that was blended and dried, and so not extruded (Example 18). The filterability after extraction of blended dried biomass was worse in comparison with dried extrudates.

EXAMPLE 19

Recovery of DHA Oil from Cryothecodinium

Biomass from 7 l of a fermentation broth (previously pasteurised, 65° C. for 1 hour) of the algae *Crypthecodinium cohnii* was harvested using a labscale centrifuge of the type lo BECXMA JM/6E. The broth was centrifuged in portions of 800 ml during 2 minutes at 5000 rpm resulting in a clear supernatant.

In total 224 g of biomass with a dry matter content of 13% was recovered. This means a biomass concentration at harvest of the fermentation broth of about 4 g/kg. To this recovered biomass 300 g of starch (ROQUETTE, batch nr. 10EV0024)) was added to increase the dry matter content. The cake recovered in this way was extruded by means of a single screw lab extruder using a universal screw and a profiled barrel. The diameter of the hole in the dieplate was 2 mm and the thickness of the dieplate was 6 mm resulting in an L/D of the dieplate of 3. The resulting smooth extrudate was dried under vacuum overnight at 50° C., resulting in a crackle dried extrudate. The dry matter content of the biomass dried in this way was about 94%.

A sample of about 180 g of the dried extrudate was extracted with hexane (initial volume/biomass ratio of 5 l/kg). After 3 hours of extraction at 60° C. the micella was filtered over a Whatman filter. The resulting extracted biomass was washed once with 1000 ml of fresh hexane. The filtered micella recovered in this way was evaporated at 68° C. ($T_{waterbath}$). In this way a crude DHA containing oil was recovered. The DHA concentration in the oil was 32.6% analysed by means of GC. The in this way recovered oil contained about 67% of tri-glycerides, 12% di-glycerides, 3.7% of sterols and about 0.2% of antifoam (NMR). An other characteristic of the oil was the level of carotenoids (0.15 mg/ml of β-carotene and 5 mg/ml of γ-carotene)

EXAMPLE 20

Recovery of Vitamin B12 from Propionibacterium sp.

Broth (heat shocked at 90° C. for 2 minutes) from a large scale fermentation of a Propionibacterium sp. (28 tons) was harvested by means of a clarifier of the type BRPX-213-8GV(ALFA LAVAL, 3–7 tons/h) at a G-factor of about 5000. The broth clarified in this way was concentrated 2.5 times by means of ultra-filtration using a ABCOR KOCH module with about 150 $m^2$ spiral-wound poly ethylene sulphone membranes with a cut-off of 5 kD (type HFK 131-VSV). The resulting ultra filtrate was diafiltrated for 500% according the concentrated volume with process water. The resulting diafiltrate was concentrated by a factor of 3 by means of vacuum evaporation.

The resulting concentrate was granulated and dried in a NIRO 250 multi stage dryer (fluidised bed spray dryer/agglomerator). The inlet air temperature of the dryer had a temperature of about 250° C. and the outlet air temperature was about 70° C. The air flow applied was about 3000 $m^3$/h. This resulted in a product temperature of about 70– 80° C. The density of the concentrate fed to the dryer was about 1050 $kg/m^3$.

A sample of about 2 g of dried granulate was used for extraction with 125 ml of about 75% of ethanol (the water content gives an optimal extraction/technical performance) in a conical flask by means of stirring during 60 minutes at ambient temperature (clear extract). After extraction the extracted biomass was filtered using a Whatman paper filter (easy filtration). The clear pink filtrate recovered in this way was analysed for vitamin B12. The resulting biomass was washed with 25 ml of about 75% ethanol. In this way about 90% of the vitamin B12 was extracted from the granulated biomass (Table 4).

TABLE 4

Data concerning extraction of vitamin B12 from Multi stage agglomerated *Propionic bacterium*.

| sample number | | g | ml | density in $kg/m^3$ | [vitamin B12] in mg/kg | total vitamin B12 in mg |
|---|---|---|---|---|---|---|
| VTB 9606²/001 | input granulate | 2.01 | — | — | 842 | 1.69 |
| VTB 9606²/002 | output extraction | 1.46 | — | — | 104.5 | 0.15 |
| VTB 9606²/003 | extract | — | 110 | 856 | 11.7 | 1.10 |
| VTB 9606²/004 | wash | — | 24 | 856 | 6.01 | 0.12 |

EXAMPLE 21

Co-extrusion *C. cohrii* and *M. alpina*

10 l of a fermentation broth of the fungus *Mortieralla alpina* and 10 l of a fermentation broth of *Crypthecodinium cohnii* were mixed together. To improve the filterability of the mixed broth $CaCl_2$ was added (end concentration of 5 g/l). The mixed broth was filtered and the resulting cake was mechanically dewatered using a typical fruit press (citrus press, HAFICO).

The cake recovered in this way was extruded by means of a single screw lab extruder using a universal transport screw in a profiled barrel and a dieplate with one hole of 2 mm. The diameter of the extrudate was about 2 mm. The extrudate recovered in this way was dried in a labscale fluid bed dryer ($T_{air}$=40° C., drying time of about one hour, airflow of 150 Nm$^3$/h, AEROMATIC MP-1). The dry matter content of the biomass dried in this way was about 92%.

A sample of about 100 g of dried extrudate was used for extraction with hexane (initial volume/biomass ratio of 4 l/kg). After 2 hours of extraction at ambient temperature the micella was recovered by means of vacuum filtration. The remaining extracted extrudate was washed with 4 volumes of fresh hexane (initial volume/biomass ratio of 4 l/kg). The washed hexane was mixed with the micella and the resulting micella was evaporated at 50° C. ($T_{water\ bath}$). In this way a crude PUFA oil was recovered containing APA (C20:4 ω6) and DHA (C22:6 ω3).

The crude oil can be refined according methods usual for edible/vegetable oils.

COMPARATIVE EXAMPLE 22

The various culturing conditions that were used to obtain the biomass and broths described in the previous examples will now be given in the following table.

| Micro organism | Product | Process type | Nutrients (g/l) | | Temperature (° C.) | pH | Time (hours) |
|---|---|---|---|---|---|---|---|
| *Fichia citerril* (-*macula citerril*) | Tetra-Acetyl-Phyto-Sphingosine (-TAPS) (extracellular) | fed batch (glucose feed) | glucose: yeast extract: salt extract: peptone: | 30 3 3 5 | 25 | 6.5–6.8 | 96 |
| *Mortierella alpina* | arachidonic acid (intracellular) | batch | glucose: yeast extract: N2NO$_1$: K$_2$HPO$_2$: MgSO$_2$.7H$_2$O: ammonium salt minerals | 50 5 5 3 0.5 | 25 | 5.5–7 | 120–168 |
| *Alakerlea triapora* | β-carotene (intracellular) | batch | Pharmedia: glucose: KH$_4$PO$_2$: MnSO$_1$.H$_2$O: soybean oil: cotton seed oil: dextrina: Triton X-100: ascorbic acid: lactic acid: thiamine-Hcl: isomlarid: | 75 10 0.5 0.1 30 30 60 1.2 6 2 2 mg 0.075% | 26–28 | 6.5 | 7 days |
| *Aspergillus terreus* ammonia | Lovastatin | fed batch (glucose + | glucose: yeast extract: KH$_2$PO$_2$: Mn$_2$SO$_1$: MgSO$_2$.7H$_2$O: CaCl$_1$.2H$_2$O: PPG (2000) (antifoam): trace elements | 20 31.3 1.0 1.4 0.1 0.1 | 28 | 6.5 3.5 | 8 days |

| Micro organism | Product | Process type | Nutrients (g/l) | | Temperature (° C.) | pH | Time (hours) |
|---|---|---|---|---|---|---|---|
| *Propionlbacterium sp.* | Vitamin B$_{12}$ (intracellular) | fed batch lanacerobe, (glucose feed + after 4 days: 10 mg/l 5,6-dimethylbenzlmldasole) | glucose: corn steep liq.: (PH$_1$)$_3$SO$_2$: KH$_2$PO$_1$: Na$_2$HPO$_2$.12H$_2$O: MgSO$_4$.7H$_2$O: minerals Ca pantothenate: | 10 60 16 0.4 1.5 0.5 10 mg | 30 | 5–7.5 | 168 |

-continued

| Micro organism | Product | Process type | Nutrients (g/l) | | Temperature (° C.) | pH | Time (hours) |
|---|---|---|---|---|---|---|---|
| Cypthecadanium cotonil | Docaebenoacoic acid (-DEA) (intracellular) | fed batch (68 g/l glucoma + 24 g/l yeast extract) | Ocean* artificial maenater: (instant) yeast extract: glucose: | 250 6 12 | 20–28 | 7–7.8 | 70–80 |

REFERENCES CONCERNING FERMENTATION TECHNIQUES

Maister H. G., Rogovin S. P., Stodola F. H., Wickerham L. J., "Formation of Extracellular Sphingolipide by Microorganisms. IV. Pilot-Plant Production of Tetraacetylphytosphingosine by *Hansenula ciferrii*". Appl. Microbiol., 10, 401-406. (1962)

Zu-Yi Li, Yingyin Lu, Yadwad V. B., Ward O. P., "Process for Production of Arachidonic Acid Concentrate by strain of *Mortierella alpina*"

Can. J. Biochem. Eng. 73, 135–139 (1995) Finkelstein M., Huang C—C., Byng C. S., Tsau B–R., Leach J., "*Blakeslea trispora* mated culture capable of increased beta-carotene production" U.S. Pat. No. 5,422,247 (1995)

Kojima I., Kouji K., Sato H., Oguchi Y., "Process for the producing Vitamin $B_{12}$ by the fermentation technique, and Vitamin $B_{12}$-producing microorganism". U.S. Pat. No. 4,544,633 (1985)

Kyle D. J., Reeb S. E., Sicotte V. J., "Production of decosahexaenoic acid by dinoflagellates". U.S. Pat. No. 5,407,957 (1995).

EXAMPLE 23

Analysis of Crude and Refined Oil

Batches of crude oil had been prepared by the methods described in Example 1 (fluidized bed drying and hexane extraction).

All analyses which are applied on the oils are performed according to procedures described by the American Oil Chemist Society (AOCS). The tri-, di-, and monoglyceride and the phospholipid contents are determined by H-NMR using a 600 MHz instrument.

The crude oil had the following composition:

| batch | | a | b | c |
|---|---|---|---|---|
| triglycerides | (%) | 96.6 | 96.5 | 96.6 |
| acid value | mg/g | 1.7 | 0.3 | 0.2 |
| peroxide value | meq/kg | 2.7 | 1.3 | 1.3 |
| anisidine value | | <1.0 | 0.3 | 0.1 |

The crude oil was refined by the standard methods as known in the edible oil processing.

Briefly, the oil was gently heated to 80–90° C., under exclusion of air entrapment. To the oil a diluted solution of NaOH was added (125% of the stoichiometric amount equivalent to the amount of free fatty acids). After 30 minutes reaction time the water phase was separated by centrifuging. The oil was washed with water until a neutral reaction of phenolphthalein. (For this purpose 3 washings with 10% of the oil volume were sufficient). The waterlayers were removed by centrifugation. After the last wash step the oil was dried in vacuo at 70° C. The dried oil was bleached by the addition of the bleaching earth Tonsil Supreme FF. (2% on weight basis was added). The bleaching earth was contacted during one hour at 60° C. at a pressure of 10–15 mbar. After the reaction time, the bleaching earth was removed by filtering on a leaf filter at a pressure of 1 bar (with nitrogen). The filtered oil was batch deodorised in vacuum at 180° C. at 2–5 mbar, during 2 hours. Steam was used as stripping medium. The steam in this way was formed in situ from water added to the oil. After the reaction time the oil was cooled. The pressure in the reactor was brought to 1 bar by the addition of nitrogen gas.

The result of this process was a clear oil with the following composition:

| batch | | a | b | c |
|---|---|---|---|---|
| phospholipids | (%) | <0.05 | <0.05 | <0.05 |
| triglycerides | (%) | 96.6 | 96.5 | 96.6 |
| diglycerides | (%) | 1.6 | 1.3 | 1.0 |
| acid value | mg/g | 0.2 | 0.15 | 0.1 |
| peroxide value | meq/kg | 1.6 | 0.8 | 0.4 |
| anisidine value | | 4.1 | 1.9 | 3.1 |
| Rancimat induction time: | | | | |
| 130° C. (hours) | | 2.5 | | |
| 100° C. (hours) | | >4 | >4 | >4 |
| 80° C. (hours) | | >10 | >10 | >10 |

What is claimed is:

1. A process for the isolation of one or more compound(s) from a microbial biomass, the process comprising:
  a) culturing microorganisms in a fermentation broth under conditions whereby the microorganisms produce the compound;
  b) pasteurising either the fermentation broth or a microbial biomass derived therefrom; and
  c) extracting, isolation or recovering the compound from the microbial biomass.

2. A process according to claim 1 wherein the pasteurisation at least partially inactivates one or more compound degrading substances either in the biomass or in the broth.

3. A process according to claim 2 wherein the substance is a protease or a triglyceride degrading enzyme.

4. A process according to claim 3 wherein the enzyme is a lipase, a phospholipase, or a lipoxygenase.

5. A process according to claim 1 wherein pasteurisation comprises heating at from 50 to 100° C.

6. A process according to claim 5 wherein the heating is at from 65 to 95° C.

7. A process according to claim 5 wherein the heating is for from 30 to 90 minutes.

8. A process according to claim 1 wherein the fermentation broth is pasteurised while still in the fermentation vessel.

9. A process according to claim 1 wherein pasteurisation takes place after fermentation has finished.

10. A process according to claim 1 wherein the compound comprises a triglyceride.

11. A process according to claim 1 wherein the compound comprises at least one polyunsaturated fatty acid (PUFA).

12. A process according to claim 8 wherein, after pasteurisation, the fermentation broth is dewatered and/or filtered to produce the microbial biomass.

13. A process according to claim 12 wherein the biomass is treated, if necessary, to give a dry matter content of from 25 to 80%.

14. A process according to claim 13 wherein the resulting biomass is granulated into granular particles, and the granular particles are then dried.

15. A process for the isolation of at least one polyunsaturated fatty acid (PUFA) from a microbial biomass, the process comprising:

a) culturing microorganisms in a fermentation broth under conditions whereby the microorganisms produce the PUFA;

b) pasteurising either the fermentation broth or a microbial biomass derived therefrom; and c) extracting, isolating or recovering the PUFA from the microbial biomass.

16. A process according to claim 15 wherein the pasteurisation at least partially inactives one or more PUFA degrading substances present either in the biomass or in the broth.

17. A process according to claim 16 wherein the substance is a protease or a triglyceride degrading enzyme.

18. A process according to claim 17 wherein the enzyme is a lipase, a phospholipase, or a lipooxygenase.

19. A process according to claim 15 wherein pasteurisation comprises heating at from 50 to 100° C.

20. A process according to claim 19 wherein the heating is at from 65 to 95° C.

21. A process according to claim 19 wherein the heating is for from 30 to 90 minutes.

22. A process according to claim 15 wherein the fermentation broth is pasteurized while still in the fermentation vessel.

23. A process according to claim 15 wherein pasteurisation take place after fermentation has finished.

24. A process according to claim 15 wherein the PUFA is in the form of a triglyceride.

25. A process according to claim 15 wherein after pasteurisation, the fermentation broth is dewatered and/or filtered to produce the microbial biomass.

26. A process according to claim 25 wherein the biomass is treated, if necessary, to give a dry matter content of from 25 to 80%.

27. A process according to claim 26 wherein the resulting biomass is granulated into granular particles, and the granular particles are the dried.

28. A composition comprising granular particles, the particles having been formed by granulating a microbial biomass containing at least one polyunsaturated fatty acid (PUFA).

29. A composition comprising dried granules formed by drying granular particles according to claim 28.

30. A PUFA or a microbial oil which has been extracted or isolated by a process according to claim 15.

31. A PUFA or a microbial oil which has been prepared from the dried granules of claim 29.

* * * * *